(12) United States Patent
Urwyler et al.

(10) Patent No.: US 6,673,925 B2
(45) Date of Patent: Jan. 6, 2004

(54) METHOD OF PRODUCING THIOBARBITURIC ACID DERIVATIVES

(75) Inventors: Bernhard Urwyler, Therwil (CH); Thomas Rapold, Wallbach (CH); Marco Passafaro, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 6 days.

(21) Appl. No.: 09/936,330

(22) Filed: Aug. 20, 2001

(65) Prior Publication Data

US 2002/0095037 A1 Jul. 18, 2002

Related U.S. Application Data

(63) Continuation of application No. PCT/EP00/00872, filed on Feb. 3, 2000.

(30) Foreign Application Priority Data

Feb. 5, 1999 (CH) ............................................... 0224/99

(51) Int. Cl.[7] ................... C07D 239/02; C07D 401/00; A61K 31/515
(52) U.S. Cl. ...................... 544/300; 544/299; 544/302; 514/270; 514/271
(58) Field of Search .................. 544/300, 299, 544/302; 514/270, 271

(56) References Cited

U.S. PATENT DOCUMENTS

| | | | |
|---|---|---|---|
| 3,931,180 A | 1/1976 | Muhle et al. | 260/256.4 |
| 3,991,191 A | 11/1976 | Winkelmann et al. | 424/251 |
| 4,057,634 A | 11/1977 | Winkelmann et al. | 424/250 |
| 4,932,999 A | 6/1990 | Saito et al. | 71/92 |

FOREIGN PATENT DOCUMENTS

| | | |
|---|---|---|
| EP | 0 529 631 | 8/1992 |
| EP | 0 547 411 | 11/1992 |
| EP | 0 565 951 | 3/1993 |
| EP | 0 315 889 | 11/1998 |

OTHER PUBLICATIONS

Krishnamurthy, S. et. al., "Rapid and Selective Reduction of Functionalized Aromatic Disulfides . . . ", Journal of Organic Chemistry, 1989, vol. 54, 4458–4462.*
Hubsch et al. Helvet. Chim Acta, 72, 1989, 744–755.
Hubsch et al. Biochem. And Clinical Aspects of Pteridines, London, 5, 1987, 25–32.
Greenbaum et al., JACS, 76, 1954, 2899–2902.
Koppel et al., J. Org. Chem., 26, 1961, 762–803.
Hubsch et al., Helvet. Chim. Acta, 72, 1989, 738–743.

* cited by examiner

Primary Examiner—Mukund J. Shah
Assistant Examiner—Tamthom N. Truong
(74) Attorney, Agent, or Firm—Thomas Hamilton

(57) ABSTRACT

Method of producing thiobarbituric acid derivatives of formula I

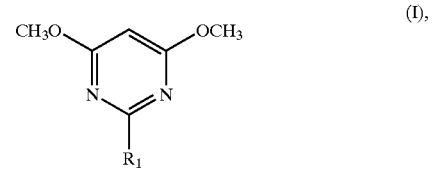

wherein
$R_1$ is SH, $S^-M^+$ or $CH_3S$—, and $M^+$ is an alkali metal ion, by hydrogenolysis of a compound of formula II

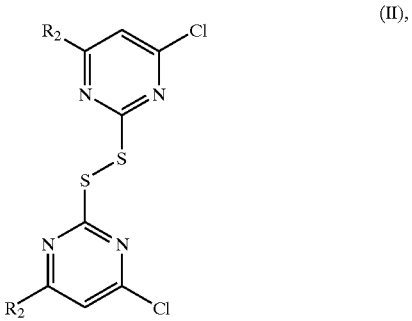

wherein $R_2$ is chlorine or $CH_3O$—, with
a) a hydrogenolysis agent in the presence of an inert solvent and by a direct reaction of the hydrogenolysis product with an alkali metal methylate in methanol, or
b) with a hydrogenolysis agent in the presence of an inert solvent and in the presence of a methylation reagent, and subsequently with an alkali metal methylate in methanol, as well as the use of these compound of formula I in the production of 7-[(4,6-dimethoxy-pyrimidin-2-yl)thio]-3-methylphthalide.

13 Claims, No Drawings

METHOD OF PRODUCING THIOBARBITURIC ACID DERIVATIVES

This application is a continuation of international application PCT/EP00/00872, filed Feb. 3, 2000.

The present invention relates to a new method of producing specifically substituted thiobarbituric acid derivatives.

J. Org. Chem. 26, 792 (1961) describes the possible pyrimidine derivatives which are substituted in the 2-, 4- and 6-positions by hydrogen, hydroxy, amino and thiole groups, it describes the possibility of obtaining them synthetically and their ability to be used in the preparation of further derivatives.

For example, the synthesis of 4,6-dichloro-2-(methylthio)pyrimidine from thiobarbituric acid by means of methylation with dimethylsulphate (DMS) in a basic medium with subsequent chlorination of the 2-(methylthio)-4,6-pyrimidinediol, formed as an intermediate, with phosphorus oxychloride is described on the one hand, and on the other hand the substitutability of the chlorine atoms in the 4- and 6-positions of the pyrimidine ring using sodium hydrogen sulphide in ethanol to form the corresponding 4,6-pyrimidinethiole.

EP-A-0 529 631 discloses the production of 2-(methylthio)-disodium barbiturate from thiourea and malonic acid dimethyl ester in the presence of sodium methanolate, and the methylation of the disodium thiobarbiturate formed as an intermediate, with methyl bromide.

J. Am. Chem. Soc. 76, 2899 (1954) describes on the one hand the production of bis-(2,4-dimethoxy-6-pyrimidinyl)-disulphide from 2,4-dimethoxy-6-pyrimidinethiole using hydrogen peroxide in dioxane, and on the other hand the cleavage thereof by reduction with lithium aluminium hydride in absolute ether to form the corresponding 2,4-dimethoxy-6-pyrimidinethiole in a yield of 76%.

In Helv. Chim. Acta 72, 744 (1989), the production of bis-(4,6-dichloropyrimidin-2-yl)-disulphide from 2-thiobarbituric acid with phosphorus oxychloride and N,N-diethylaniline is described, and it is pointed out therein at the same time that the disulphide formed cannot be converted into the monomeric uracil derivative either by acid- or base-catalysed hydrolysis or by reductive hydrolysis.

EP-A-0 547 411 discloses the production of 4,6-dialkoxy-2-alkylmercapto-pyrimidines by cyclising cyanimidates in the presence of hydrogen halide to form 4,6-dialkoxy-2-halopyrimidine and reacting the latter compound with sodium thiolate.

DE-A-2 412 854 describes the production of 2-alkylthio-4-methoxy-6-hydroxypyrimidine by means of methylation of 2-alkylthio-4,6-dihydroxypyrimidine using dimethylsulphate.

Helv. Chim. Acta 72, 738 (1989) describes, in a two-stage process, the selective basic hydrolysis of the chlorine substituent in 2-position of 2,4,6-trichloropyrimidine and the subsequent nucleophilic substitution of the remaining chlorine substituents in 4- and 6-position with methanol.

Furthermore, DE-A-4 408 404 and DE-A-2 248 747 describe the conversion of 2-hydroxy-4,6-dialkoxypyrimidine with phosphorus oxychloride and with catalytic amounts of amine hydrochloride or with phosphorus pentachloride to form 2-chloro-4,6-dialkoxypyrimidine.

All these described methods of producing specifically substituted (thio-)barbituric acid derivatives are partly complex in operation via several reaction steps, since on the one hand certain substituents at defined positions of the pyrimidine ring have practically the same reactivity and cannot therefore be substituted selectively, or on the other hand they are sluggish in reaction towards nucleophilic reagents or even have remarkable stability, and, if at all, they only react under extreme reaction conditions, such as in a pressurised container and at elevated temperatures (see e.g. J. Org. Chem. 26, 794 (1961) and Helv. Chim. Acta 72, 745 (1989). The observed product yields and product purities are consequently frequently unsatisfactory for large-scale production methods. In addition, the isolation and purification processes are uneconomical and are linked with complex apparatus.

It has surprisingly now been found that specifically substituted 4,6-dimethoxy-2-thiobarbituric acid, 4,6-dimethoxy-2-sodium thiobarbiturate and 4,6-dimethoxy-2-methylthiopyrimidine can be easily produced in high yield and purity, economically and ecologically, most advantageously in a one-pot process, avoiding the above-described disadvantages of the disclosed methods, directly from bis-(4,6-disubstituted) 2-pyrimidine disulphides, by hydrogenolysing the latter compound and methylating the hydrogenolysis product directly without isolation either with an alkali metal alcoholate or with a methylation reagent, and then reacting the thiomethylation product with an alkali metal alcoholate.

An object of the present invention is thus a method of producing thiobarbituric acid derivatives of formula I

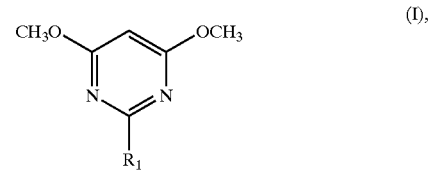

wherein
  $R_1$ is SH, $S^-M^+$ or $CH_3S-$, and $M^+$ is an alkali metal ion, by hydrogenolysis of a compound of formula II

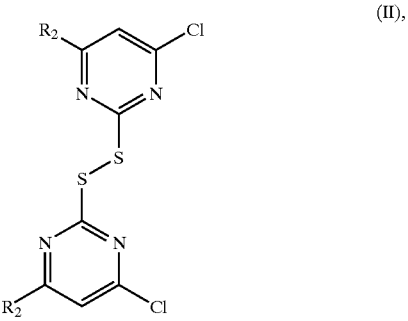

wherein $R_2$ is chlorine or $CH_3O-$, with
  a) a hydrogenolysis agent in the presence of an inert solvent and by a direct reaction of the hydrogenolysis product with an alkali metal methylate in methanol, or
  b) with a hydrogenolysis agent in the presence of an inert solvent and in the presence of a methylation reagent, and subsequently with an alkali metal methylate in methanol.

The hydrogenolysis agents which are suitable for the hydrogenolytic cleavage of the compound of formula II are e.g. boron hydrides, diborane, alkali metal aluminium hydrides and hydrogen. Of these, those that are especially suitable are alkali metal borohydrides, diborane, lithium aluminium hydride and hydrogen in the presence of a noble metal catalyst.

Particularly suitable hydrogenolysis agents are alkali metal borohydrides and hydrogen in the presence of a noble metal catalyst, especially sodium borohydride and hydrogen in the presence of palladium or platinum.

These hydrogenolysis agents are conveniently used in equimolar amounts or in a slight excess of 5–15 mol %, based on the compound of formula II.

The hydrogenolysis reaction of the compound of formula II according to variant a) or b) is carried out at a reaction temperature of 0° to 60° C.

The solvents that are suitable for the hydrogenolysis reaction of the compound of formula II according to variant a) or b) are e.g. ketones, amides, nitriles, aliphatic hydrocarbons, ethers, alcohols, alcohol-water mixtures and mixtures of these solvents. Preference is given to acetone, N,N-dimethylformamide (DMF), 1-methyl-2-pyrrolidone (NMP), acetonitrile, dioxane, tetrahydrofuran, methanol and methanol-water mixture.

Particularly preferred are acetone, N,N-dimethylformamide, methanol, dioxane and tetrahydrofuran.

A further characteristic of the method according to the invention is that the hydrogenolysis according to variant a) or b) takes place continuously, i.e. as a 'one-pot reaction' without isolation of intermediate products.

The hydrogenolysis product of formula IV which is formed directly according to variant a)

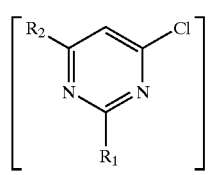

(IV), wherein $R_1$ is SH or $S^-M^+$; $M^+$ is an alkali metal ion and $R_2$ is defined as given for formula I, is unstable and is not isolated.

The hydrogenolysis product of formula III which is formed directly according to variant b)

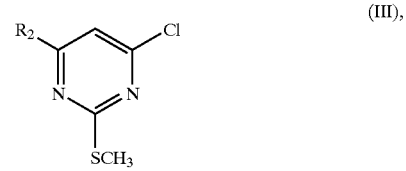

wherein $R_2$ is defined as given for formula I, is stable and may be isolated if required.

Reaction scheme 1 illustrates these reactions.

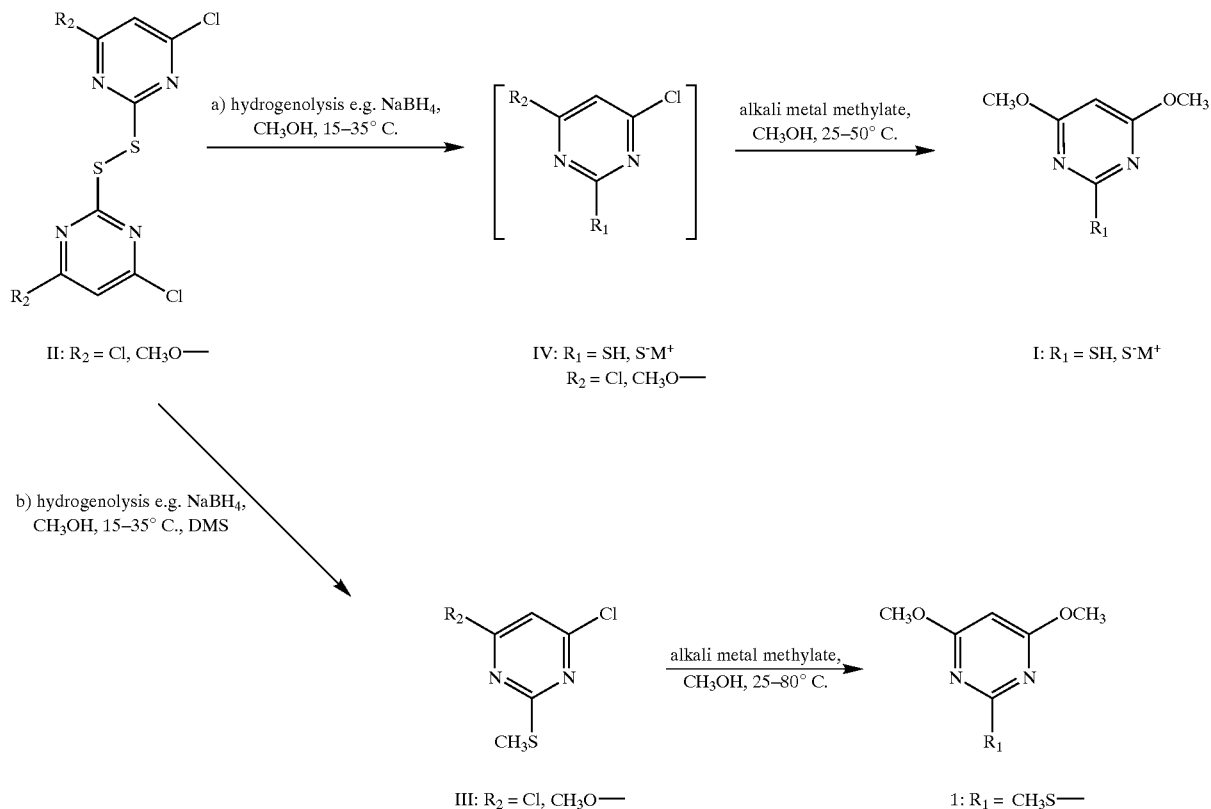

If diborane or hydrogen is used as the hydrogenolysis agent in the presence of a noble metal catalyst, then according to variant a) a compound of formula IV, in which $R_1$ is SH, is obtained as the primary unstable hydrogenolysis product. If an alkali metal borohydride or alkali metal aluminium hydride is used as the hydrogenolysis agent, then according to variant a) a compound of formula IV, in which $R_1$ is $S^-M^+$ and $M^+$ is an alkali metal ion, is obtained as the primary unstable hydrogenolysis product.

In a preferred variant a) of the hydrogenolysis reaction according to the invention, the compound of formula II in dry methanol, N,N-dimethylformamide or acetonitrile is mixed at 15° to 35° C. with a small excess of 5–10 mol % of sodium borohydride as required, then stirred for 0.5 to 3 hours and afterwards at the same reaction temperature a small excess of sodium methylate in methanol (5–10 mol %)

is added as required, and this reaction mixture is heated lightly to 25° to 50° C. whilst stirring. After cooling the reaction mixture, the crude product obtained can either be used directly for further reactions, or can be isolated by concentrating the crude product and prepared in pure form by conventional purification methods, such as recrystallisation. The yields are generally in the range of 20 to ≧90% of theory (depending on the solvent used).

In a preferred variant b) of the hydrogenolysis reaction according to the invention, the compound of formula II in dry methanol, N,N-dimethylformamide or acetonitrile is mixed at 15° to 25° C. with one molar equivalent of dimethylsulphate (DMS), based on the compound of formula II, then at 50 to 35° C. with a small excess of 5–10 mol % of sodium borohydride as required and subsequently stirred (ca. 1–3 hours) until the disulphide of formula II has hydrogenolysed and methylated to the compound of formula III

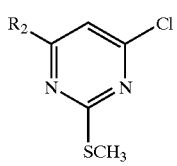

(III), wherein $R_2$ is chlorine or $CH_3O—$, and then, at the same reaction temperature, an excess of sodium methylate in methanol (5–50 Mol %) is added and this reaction mixture is heated whilst stirring to 25° to 80° C. until the reaction is complete. After cooling the reaction mixture, the crude product obtained can either be used directly for further reactions, or the salts formed can be filtered, the filtrate concentrated and the crude product isolated and prepared in pure form by conventional purification methods, such as recrystallisation. The yields are generally in the range of 80 to ≧90% of theory.

The compounds of formula I which are preferably produced by the method according to the invention are 4,6-dimethoxy-2-pyrimidine sodium mercaptid and 4,6-dimethoxy-2-methyl-mercaptopyrimidine.

The starting compounds of formula II, as well as all the hydrogenolysis agents employed, are known or may be produced by known methods. For example, Helv. Chim. Acta 72, 744 (1989) describes the production of bis-(4,6-dichloropyrimidin-2-yl)-disulphide ($R_2$=chlorine in compound of formula II) from 2-thiobarbituric acid with phosphorus oxychloride and N,N-diethylaniline. Methoxylation of the bis-(4,6-dichloropyrimidin-2-yl)-disulphide with an excess of alkali metal methylate readily leads to substitution of each chlorine substituent at the two pyrimidine rings and yields the compound of formula II, wherein $R_2$ signifies $CH_3O—$ (see also J. Am. Chem. Soc. 76, 2899 (1954)).

The method according to the invention is distinguished from known methods in that 1) it yields the 4,6-dimethoxypyrimidine-2-thiole derivatives in high purity and yield under mild reaction conditions,
2) it enables the reaction to progress rapidly,
3) it may be conceived as a 'one-pot reaction',
4) it allows easy, direct and economically and ecologically advantageous access to 4,6-dimethoxypyrimidine-2-thiole derivatives, and
5) it allows 'in situ' subsequent reactions, such as oxidation, to form corresponding 2-(methylsulphonyl)-pyrimidine derivatives.

The advantages of the present method over the known methods are therefore:

1) it is particularly suitable for large-scale applications,
2) it avoids the usage of complex separation and purification steps, and
3) it is possible to further process the formed 4,6-dimethoxy-pyrimidine-2-thiole derivatives of formula I in a one-pot process without changing the solvents and thereby reduce the solvent waste material and the need for complex apparatus.

The 4,6-dimethoxypyrimidine-2-thiole derivatives of formula I which are produced according to the invention are used especially as intermediates in the production of 7-[(4,6-dimethoxy-pyrimidin-2-yl)thio]-3-methylnaphthalide, as described for example in EP-A-0 447 506.

In a first reaction step, therefore, the 4,6-dimethoxypyrimidine-2-thiole derivatives of formula I which are produced according to the invention

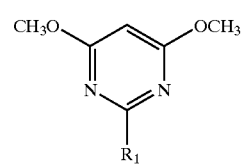

(I), wherein $R_1$ is $CH_3S—$, are reacted with an oxidation agent such as peroxides, for example hydrogen peroxide, in acetic acid and in the presence of an alkali metal tungstate such as sodium tungstate, or chlorine gas, and the 4,6-dimethoxy-2-(methylsulphonyl)pyrimidine thus obtained is reacted together with 7-mercapto-3-methylphthalide in a substitution reaction.

In a first reaction step, therefore, the 4,6-dimethoxypyrimidine-2-thiole derivatives of formula I which are produced according to the invention

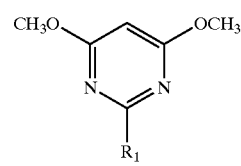

(I), wherein $R_1$ is SH or $S^-M^+$ and $M^+$ is an alkali metal ion, are reacted with a methylation agent such as dimethylsulphate (DMS), then with an oxidation agent such as peroxides, for example hydrogen peroxide, in acetic acid and in the presence of alkali metal tungstate such as sodium tungstate, or chlorine gas, and the 4,6-dimethoxy-2-(methylsulphonyl) pyrimidine thus obtained is reacted with 7-mercapto-3-methylphthalide.

The above process variants for the production of 7-[(4,6-dimethoxypyrimidin-2-yl)thio]-3-methylnaphthalide are illustrated in the following reaction scheme 2.

Reaction scheme 2

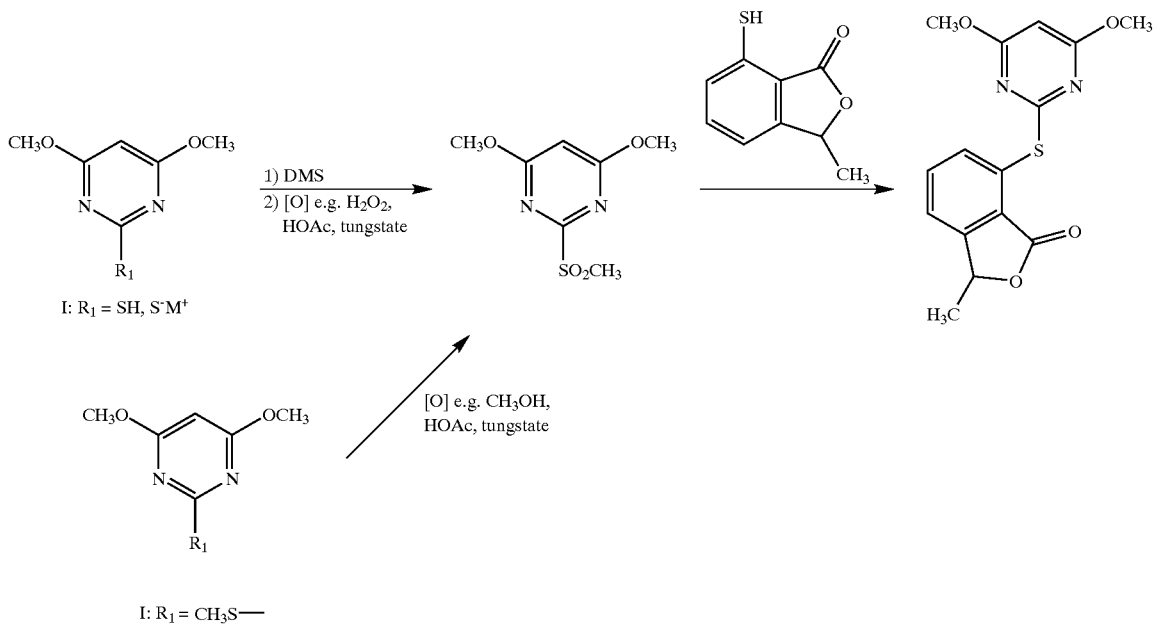

I: $R_1$ = SH, S⁻M⁺

I: $R_1$ = CH$_3$S—

According to reaction scheme 2, in a first reaction step 4,6-dimethoxy-2-pyrimidinethiole or the alkali metal thiolate thereof is methylated to the intermediate 4,6-dimethoxy-2-methylthio-pyrimidine. This methylation with dimethylsulphate (DMS) is conveniently effected in an aqueous-basic medium, optionally in the presence of a polar organic solvent such as alcohols, at temperatures of 0° to 40° C. The subsequent oxidation, for example with hydrogen peroxide, may take place either directly in the same solvent or in organic acids such as alkanecarboxylic acids, for example acetic acid and in the presence of alkali metal tungstate, e.g. sodium tungstate, or with chlorine gas, to yield 4,6-dimethoxy-2-(methylsulphonyl)pyrimidine.

In reaction scheme 2, the desired 4,6-dimethoxy-2-(methylsulphonyl)pyrimidine may be obtained from 4,6-dimethoxy-2-methylmercapto-pyrimidine directly by oxidation e.g. with hydrogen peroxide in alcohols, adding organic acids, and in the presence of alkali metal tungstate.

Methylation and oxidation reactions of this kind are described for example in DE-A-2 412 854, DE-A-3 324 399, EP-A-0 033 195, Z. Chem. 17(392), 63 (1977), Chem. Soc. 16(6), 489 (1995) and J. Org. Chem. 26, 792 (1961).

The subsequent reaction of the formed 4,6-dimethoxy-2-(methylsulphonyl)pyrimidine with 7-mercapto-3-methylphthalide in reaction scheme 2 conveniently takes place in an inert organic solvent such as ethers, ketones, nitriles and amides, for example tetrahydrofuran, butanone, acetonitrile and N,N-dimethylformamide, at temperatures of 0° to 160° C. Substitution reactions of this kind are described e.g. in EP-A-0 447 506.

The following examples further illustrate the method according to the invention.

EXAMPLE P1
Preparation of 4,6-dimethoxy-2-methylthiobarbituric Acid 1.8 g of bis-(4,6-dichloro-2-pyrimidine)-disulphide are dissolved at 22° C. in 30 g of N,N-dimethylformamide. After adding 1.26 g of dimethylsulphate (DMS), the solution is mixed with 0.19 g of sodium borohydride at 5° to 35° C. and stirred for ca. 1 hour, until all the educt from this step has been methylated to 4,6-dichloro-2-methylthiobarbituric acid (analysis by thin-layer chromatography). Subsequently, 5.5 g of methanol/sodium methylate (30%) are added at 25° C. and the reaction mixture heated to 50° C. At this temperature, stirring is continued until all the 4,6-dichloro-2-methylthiobarbituric acid has reacted. The desired title compound can either be mixed with water, cooled and isolated by filtration, or can be further used directly for the next reaction.

EXAMPLE P2
Preparation of 4,6-dimethoxy-2-(methylsulphonyl) pyrimidine 30 g of water are added to the above reaction mixture and the reaction mixture is adjusted to pH 3–4 with acetic acid. After adding 0.01 g of tetrabutylammonium bromide and 0.01 g of sodium tungstate, 3.4 g of hydrogen peroxide (30%) are dispensed in over 30 minutes at 60°–70° C. After stirring for ca. 1 hour at 60°–70° C., oxidation to the corresponding methylsulphonyl is complete. The reaction mixture is cooled to 0° C., mixed with ca. 15 g of water and the precipitated product is isolated by filtration. The desired target compound is obtained in pure form in a yield of 80–90%.

EXAMPLE P3
Preparation of 4,6-dichloro-2-methylthiobarbituric Acid

In an agitating autoclave, a solution of 2.5 g of 4,6-dichloro-2-pyrimidine-disulphide and 50 ml of methanol is mixed with 1.86 g of 2,6-lutidine and 2.2 g of dimethylsulphate. Subsequently, 0.25 g of sulphidised Pd-carbon catalyst (Engelhard) are added and hydrogenation is carried out for 9 hours at 22° C. and at a hydrogen pressure of 20 bars. After cooling and rendering the agitating autoclave inert with nitrogen gas, the catalyst is filtered off and washed with methanol. After working up by column chromatography, 1.08 g of the desired title compound is obtained in a yield of 82% of theory.

$^1$H-NMR (CDCl$_3$, 400 MHz): 7.08 ppm (s, 1H).

What we claim is:

1. Method of producing thiobarbituric acid derivatives of formula I

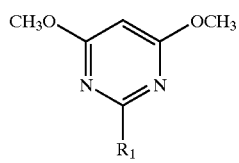

wherein
R$_1$ is SH, S$^-$M$^+$ or CH$_3$S—, and M$^+$ is an alkali metal ion, by hydrogenolysis of a compound of formula II

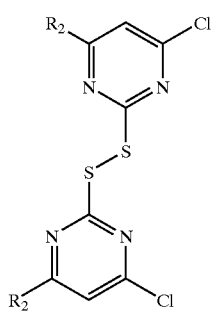

wherein R$_2$ is chlorine or CH$_3$O—, with
a) a hydrogenolysis agent in the presence of an inert solvent and by a direct reaction of the hydrogenolysis product with an alkali metal methylate in methanol, or
b) with a hydrogenolysis agent in the presence of an inert solvent and in the presence of a methylation reagent, and subsequently with an alkali metal methylate in methanol; wherein, hydrogenolysis according to variant a) or b) is carried out at a reaction temperature of 0° to 60° C.

2. Method according to claim 1, in which the hydrogenolysis agent is selected from the group consisting of borohydrides, diborane, alkali metal aluminium hydrides and hydrogen in the presence of palladium or platinum.

3. Method according to claim 2, in which the hydrogenolysis agent is selected from the group consisting of an alkali metal borohydride, diborane, lithium aluminium hydride and hydrogen in the presence of palladium or platinum.

4. Method according to claim 3, in which the hydrogenolysis agent is selected from the group consisting of an alkali metal borohydride and hydrogen in the presence of palladium or platinum.

5. Method according to claim 4, in which the hydrogenolysis agent is selected from the group consisting of sodium borohydride and hydrogen in the presence of palladium or platinum.

6. Method according to claim 1, in which the hydrogenolysis agent is used in equimolar amounts or in a slight excess of 5–15 mol %, based on the compound of formula II.

7. Method according to claim 1, in which hydrogenolysis according to variant a) or b) is carried out in the presence of ketones, amides, nitriles, aliphatic hydrocarbons, ethers, alcohols, alcohol-water mixtures or in mixtures of these solvents.

8. Method according to claim 7, in which acetone, N,N-dimethylformamide, 1-methyl-2-pyrrolidone, acetonitrile, dioxane, tetrahydrofuran, methanol or a methanol-water mixture is used as the solvent.

9. Method according to claim 8, in which acetone, N,N-dimethylformamide, methanol, dioxane or tetrahydrofuran is used.

10. Method according to claim 1, in which hydrogenolysis according to variant a) or b) is carried out continuously, i.e. as a 'one-pot reaction'.

11. Method according to claim 1, in which the compound of formula II in dry methanol, N,N-dimethylformamide or acetonitrile is mixed at 15° to 35° C. with sodium borohydride, subsequently stirred for 0.5 to 3 hours, and afterwards at the same reaction temperature, a small excess of sodium methylate in methanol is added, and this reaction mixture is heated gently to 25° to 50° C. whilst stirring.

12. Method according to claim 1, in which the compound of formula II in dry methanol, N,N-dimethylformamide or acetonitrile is mixed at 15° to 25° C. with one molar equivalent of dimethylsulphate, based on the compound of formula II, then at 5° to 35° C. with sodium borohydride, and is subsequently stirred until the disulphide of formula II has hydrogenolysed and methylated to the compound of formula III

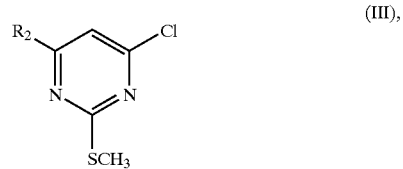

wherein R$_2$ is chlorine or CH$_3$O—, and then, at the same reaction temperature, an excess of sodium methylate in methanol is added and this reaction mixture is heated whilst stirring to 25° to 80° C.

13. Method according to claim 1 for the production of 4,6-dimethoxy-2-pyrimidine sodium mercaptide and 4,6-dimethoxy-2-methylmercapto-pyrimidine.

* * * * *